US007198777B2

(12) United States Patent
Boppart et al.

(10) Patent No.: US 7,198,777 B2
(45) Date of Patent: Apr. 3, 2007

(54) OPTICAL CONTRAST AGENTS FOR OPTICALLY MODIFYING INCIDENT RADIATION

(75) Inventors: Stephen A. Boppart, Champaign, IL (US); Daniel L. Marks, Urbana, IL (US); Kenneth S. Suslick, Champaign, IL (US); Farah Jean-Jacques Toublan, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 277 days.

(21) Appl. No.: 10/463,835

(22) Filed: Jun. 17, 2003

(65) Prior Publication Data

US 2004/0258762 A1  Dec. 23, 2004
US 2006/0121123 A9  Jun. 8, 2006

(51) Int. Cl.
*A61K 49/00* (2006.01)
(52) U.S. Cl. .................. 424/9.6; 424/1.11; 424/9.1; 424/9.3; 424/9.4
(58) Field of Classification Search ............... 424/1.11, 424/1.29, 1.33, 1.37, 1.65, 9.1, 9.3, 9.4, 9.5, 424/9.6, 9.7, 9.8; 430/1; 600/101; 250/311, 250/338.1; 359/368, 370, 385, 656
See application file for complete search history.

(56) References Cited

U.S. PATENT DOCUMENTS

| | | | |
|---|---|---|---|
| 4,522,811 A | 6/1985 | Eppstein et al. | |
| 5,362,478 A | 11/1994 | Desai et al. | |
| 5,439,686 A | 8/1995 | Desai et al. | |
| 5,498,421 A | 3/1996 | Grinstaff et al. | |
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,560,933 A | 10/1996 | Soon-Shiong et al. | |
| 5,635,207 A | 6/1997 | Grinstaff et al. | |
| 5,639,473 A | 6/1997 | Grinstaff et al. | |
| 5,648,506 A | 7/1997 | Desai et al. | |
| 5,650,156 A | 7/1997 | Grinstaff et al. | |
| 5,665,382 A | 9/1997 | Grinstaff et al. | |
| 5,665,383 A | 9/1997 | Grinstaff et al. | |
| 5,753,261 A * | 5/1998 | Fernandez et al. ........... | 424/450 |
| 5,914,806 A | 6/1999 | Gordon, II et al. | |
| 5,930,026 A | 7/1999 | Jacobson et al. | |
| 5,972,493 A | 10/1999 | Iwasaki et al. | |
| 6,068,600 A | 5/2000 | Johnson et al. | |
| 6,156,292 A | 12/2000 | Quay | |
| 6,231,834 B1 | 5/2001 | Unger et al. | |
| 6,246,892 B1 | 6/2001 | Chance | |
| 6,246,901 B1 | 6/2001 | Benaron | |
| 6,249,271 B1 | 6/2001 | Albert et al. | |
| 6,262,706 B1 | 7/2001 | Albert et al. | |
| 6,262,833 B1 | 7/2001 | Loxley et al. | |
| 6,264,917 B1 | 7/2001 | Klaveness et al. | |
| 6,264,918 B1 | 7/2001 | Johnson et al. | |
| 6,280,704 B1 | 8/2001 | Schutt et al. | |
| 6,300,932 B1 | 10/2001 | Albert | |
| 6,312,304 B1 | 11/2001 | Duthaler et al. | |
| 6,315,981 B1 | 11/2001 | Unger | |
| 2002/0054912 A1 | 5/2002 | Kim et al. | |
| 2004/0058458 A1 | 3/2004 | Anker et al. | |

OTHER PUBLICATIONS

Ai, H., M. Fang, S. Jones &Y. Lvov, "Electrostatic layer-by-layer nanoassembly on biological microtemplates: platelets," *Biomacromolecules*, 3:560-564, 2002.
Amsden, B., "The production of uniformly sized polymer microspheres," *Pharm. Res.*, 16:1140-1143, 1999.
Amsden, B. & M. Goosen, "An examination of factors affecting the size, distribution, and release characteristics of polymer microbeads made using electrostatics," *J. Control. Release*, 43:183-196, 1997.
Barton, J., J. Hoying, & C. Sullivan, "Use of microbubbles as an optical coherence tomography contrast agent," Contrast Material Research Conference, Sep. 12-17, 1999, Woodstock, VT, in Academic Radiology 9 (Supp. 1):S52-S55, 2002.
Boppart, S., B. Bouma, C. Pitris, J. Southern, M. Brezinski & J. Fujimoto, "*In vivo* cellular optical coherence tomography imaging," *Nature Med.*, 4:861-865, 1998.
Boppart, S., B. Bouma, C. Pitris, G. Tearney, J. Southern, M. Brezinski & J. Fujimoto, "Intraoperative assessment of microsurgery with three-dimensional optical coherence tomography," *Radiology*, 208:81-86, 1998.
Boppart, S., B. Bouma, C. Pitris, G. Tearney J. Fujimoto & M. Brezinski, "Forward-imaging instruments for optical coherence tomography," *Optics Letters*, 22:1618-1620, 1997.
Boppart, S., M. Brezinski, B. Bouma, G. Tearney & J. Fujimoto, "Investigation of developing embryonic morphology using optical coherence tomography," *Devel. Biol.*, 177:54-63, 1996.
Boppart, S., M. Brezinski, C. Pitris, & J. Fujimoto, "Optical coherence tomography for neurosurgical imaging of human intracortical melanoma, *Neurosurgery*," 43:834-841, 1998.
Boppart, S., B. Bouma, M. Brezinski, G. Tearney & J. Fujimoto, "Imaging developing neural morphology using optical coherence tomography," *J. Neurosci. Meth.*, 70:65-72, 1996.
Boppart, S., G. Tearney, B. Bouma, J. Southern, M. Brezinski & J. Fujimoto, Noninvasive assessment of the developing *Xenopus* cardiovascular system using optical coherence tomography, *Proc. Natl. Acad. Sci. USA*, 94:4256-4261, 1997.
Bouma, B., G. Tearney, S. Boppart, M. Hee, M. Brezinski & J. Fujimoto, "High-resolution optical coherence tomographic imaging using a mode-locked Ti:$Al_2O_3$ laser source," *Optics Letters*, 20:1486-1488, 1995.
Bouma, B., G. Tearney, C. Compton & N. Nishioka, "High-resolution imaging of the human esophagus and stomach *in vivo* using optical coherence tomography," *Gastrointest. Endosc.*, 51:467-474, 2000.
Brezinski, M., G. Tearney, B. Bouma, J. Izatt, M. Hee, E. Swanson, J. Southern & J. Fujimoto "Optical coherence tomography for optical biopsy: properties and demonstration of vascular pathology," *Circulation*, 93:1206-1213, 1996.

(Continued)

*Primary Examiner*—Dameron L. Jones
(74) *Attorney, Agent, or Firm*—Even Law Group LLC

(57) ABSTRACT

A method of enhancing the contrast of an image of a sample, comprises forming an image of a mixture, by exposing the mixture to electromagnetic radiation. The mixture comprises the sample and microparticles. The enhancement is particularly suitable for optical coherence tomography.

25 Claims, 6 Drawing Sheets

OTHER PUBLICATIONS

Bugaj, J., S. Achilefu, R. Dorshow & R. Rajagopalan, "Novel fluorescent contrast agents for optical imaging of *in vivo* tumors based on a receptor-targeted dye-peptide conjugate platform," *J. Biomed. Opt.*, 6:122-133, 2001.

Burns, R., J. Klaunig, J. Shulok, W. Davis & P. Goldblatt, "Tumor-localizing and photosensitizing properties of hematoporphyrin derivative in hamster buccal pouch carcinoma," *Oral Surg. Oral Med. Oral Pathol.*, 61:368-372, 1986.

Caruso, F., R. Caruso, & H. Möhwald, "Nanoengineering of inorganic and hybrid hollow spheres by colloidal templating," *Science* 282:1111-1114, 1998.

Chen, Z., T. Milner, S. Srinivas, X. Wang, A. Malekafzali, M. van Gemert & J. Nelson "Noninvasive imaging of *in vivo* blood flow velocity using optical doppler tomography," *Optics Letters*, 22:1119-1121, 1997.

Christiansen, C., H. Kryvi, P. Sontum & T. Skotland, "Physical and biochemical characterization of Albunex™, a new ultrasound contrast agent consisting of air-filled albumin microspheres suspended in a solution of human albumin," *Biotechnol. Appl. Biochem.*, 19:307-320, 1994.

de Boer, J., T. Milner, M. van Germert, & S. Nelson, "Two-dimensional birefringence imaging in biological tissue by polarization-sensitive optical coherence tomography," *Optics Letters*, 22:934-936, 1997.

Decher, G., "Fuzzy Nanoassemblies: Toward layered polymeric multicomposites," *Science*, 277:1232-1237, 1997.

Desai, N., P. Soon-Shiong, M. Grinstaff, Z. Yao, P. Sandford, K. Suslick & P. Soon-Shiong, "Controlled and targeted drug delivery with biocompatible protein shell microspheres," Abstract from 20th Annual Meeting of Society of Biomolecules, Apr. 4-9, 1994, Boston, MA, *Proc. Soc. Biomaterial*, 20:112, 1994.

Dick, A., G. Adam, J. Tacke, A Prescher, T. Southon & R. Günther, "Computed tomography of experimental liver abscesses using a new liposomal contrast agent," *Invest. Radiology*, 31:194-203, 1996.

Drexler, W., U. Morgner, F. Käftner, C. Pitris, S. Boppart, X. Li, E. Ippen & J. Fujimoto, "*In vivo* ultrahigh-resolution optical coherence tomography," *Optics Letters*, 24:1221-1223, 1999.

Freeman, R., K. Grabar, K. Allison, R. Bright, J. Davis, A. Guthrie, M. Hommer, M. Jackson, P. Smith, D. Walter & M. Natan, "Self-assembled metal colloid monolayers: an approach to SERS substrates," *Science*, 267:1629-1632, 1995.

Fu, K., D. Pack, A. Klibanov, & R. Langer, "Visual evidence of acidic environment within degrading poly(lactic-co-glycolic acid) (PLGA) microspheres," *Pharmac. Res.*, 17:100-106, 2000.

Fujimoto, J., M. Brezinski, G. Tearney, S. Boppart, B. Bouma, M. Hee, J. Southern & E. Swanson, "Optical biopsy and imaging using optical coherence tomography," *Nature Medicine*, 1:970-972, 1995.

Gazelle, G., G. Wolf, G. McIntire, E. Bacon, E. Halpern, E. Cooper & J. Toner, "Nanoparticulate computed tomography contrast agents for blood pool and liver-spleen imaging," *Acad. Radiol.*, 1:373-376, 1994.

Geny, B, P. Bischoff, B. Muan, F. Piquard, J. Thiranos, E. Epailly, M. Lambrechs, A. Juelsrud-Vebner, B. Eisenmann & P. Haberey, "Safety of a new transpulmonary echocontrast agent (Albunex®) in repeated echocardiographic studies in patients," *Clin. Cardiol.*, 20:111-115, 1997.

Gram, T., "Drug absorption and distribution," in *Modern Pharmacology with Clinical Applications*. (Craig, CR, R. Stitzel, eds. Little, Brown, & Co., Inc., Boston, MA), pp. 13-24, 1997.

Grinstaff, M. & K. Suslick, "Air-filled proteinaceous microbubbles: synthesis of an echo-contrast agent," *Proc. Natl. Acad. Sci. USA*, 88:7708-7710, 1991.

Hee, M., J. Izatt, E. Swanson, D. Huang, J. Schuman, C. Lin, C. Puliafito & J. Fujimoto, "Optical coherence tomography of the human retina," *Arch. Ophthalmol.* 113:325-332, 1995.

Huang, D., E. Swanson, C. Lin, J. Schuman, W. Stinson, W. Chang, M. Hee, T. Flotte, K. Gregory, C. Puliafito & J. Fujimoto, "Optical coherence tomography," *Science*, 254: 1178-1181, 1991.

Jue, R., J. Lambert, L. Pierce & R. Traut, "Addition of sulfhydryl groups to *Escherichia coli* ribosomes by protein modification with 2-iminothiolane (methyl 4-mercaptobutyrimidate), " *Biochemistry*, 17:5399-5406, 1978.

Kim, K. K. Jang & R. Upadhye, "Hollow silica spheres of controlled size and porosity by sol-gel processing," *J. Am. Ceram. Soc.*, 74:1987-1992, 1991.

Kim, N., K. Kim, D. Payne & R. Upadhye, "Fabrication of hollow silica aerogel spheres by a droplet generation method and sol-gel processing" *J. Vac. Sci., Technol. A.*, 7:1181-1184, 1989.

Kolbeck, K., "The biomedical applications of protein microspheres," Ph.D. Doctoral Thesis, University of Illinois, Urbana-Champaign, 1999.

Korbelik, M. & G. Krosl, "Photofrin accumulation in malignant and host cell populations of various tumours," *Br. J. Cancer.*, 73:506-513, 1996.

Langer, R, "Drug delivery and targeting," *Nature*, 392:5-10, 1998.

Lasic D. and D. Papahadjopoulos, "Lipsomes revisited," *Science*, 267:1275-1276, 1995.

Lee, R. & P. Low, "Delivery of liposomes into cultured KB cells via folate receptor-mediated endocytosis," *J. Biol. Chem.*, 269:3198-3204, 1994.

Leelarasamee, N., S. Howard, C. Malanga & J. Ma, "A method for the preparation of polylactic acid microcapsules of controlled particle size and drug loading," *J. Microencapsul.*, 5:147-157, 1988.

Li, X., S. Boppart, J. Van Dam, R. Mashimo, M. Mutinga, W. Drexler, M. Klein, C. Pitris, M. Krinsky, M. Brezinski & J. Fujimoto, "Optical coherence tomography: advanced technology for the endoscopic imaging of Barrett's Esophagus," *Endoscopy*, 32:921-930, 2000.

Liu, K., M. Grinstaff, J. Jiang, K. Suslick, H. Swartz & W. Wang, "In vivo measurement of oxygen concentration using sonochemically synthesized microspheres," *Biophys. J.*, 67:896-901, 1994.

Lvov, Y., R. Price, B. Gaber & I. Ichinose, "Thin film nanofabrication via layer-by-layer adsorption of tubule halloysite, spherical silica, proteins and polycations," *Colloids Surf. A*, 198-200:375-382, 2002.

Lvov, Y. & R. Price, "Nanoparticle/polyion assembly on microtemplates (lipid tubules and latex spheres)," *Colloids Surf. B*, 23:251-256, 2002.

Mathias, C., S. Wang, R. Lee, D. Waters, P. Low & M. Green, "Tumor-selective radiopharmaceutical targeting via receptor-mediated endocytosis of Gallium-67-deferoxamine-folate," *J. Nucl. Med.*, 37:1003-1008, 1996.

McNamara III, W., Y. Didenko & K. Suslick, "Sonoluminescence temperatures during multibubble cavitation," *Nature*, 401:722-775,1999.

Möhwald, H., "From Langmuir monolayers to nanocapsules," *Colloids. Surf. A*, 171:25-31, 2000.

Peters, T., "All about albumin," in *Biochemistry, Genetics, and Medical Applications*, (Academic Press, New York), 1996.

Pinkerton, K., J. Gallen, R. Mercer, V. Wong, C. Plopper & B. Tarkington, "Aerosolized fluorescent microspheres detected in the lung using confocal scanning laser microscopy," *Micros. Res. Tech.*, 26:437-443, 1993.

Pitris, C., A. Goodman, S. Boppart, J. Libus, J. Fujimoto & M. Brezinski, "High resolution imaging of gynecological neoplasms using optical coherence tomography," *Obstet. Gynecol.*, 93:135-139, 1999.

Pitris, C., C. Jesser, S. Boppart, D. Stamper, M. Brezinski & J. Fujimoto, "Feasibility of optical coherence tomography for high-resolution imaging of human gastrointestinal tract malignancies," *J. Gastroenterol.*, 35:87-92, 2000.

Profio, A. & D. Doiron, "Transport of light in tissue in photodynamic therapy," *Photochem. Photobiol.*, 46:591-599, 1987.

Puliafito, C., M. Hee, C. Lin, E. Reichel, J. Schuman, J. Duker, J. Izatt, E. Swanson & J. Fujimoto, "Imaging of macular diseases with optical coherence tomography," *Ophthalmology*, 102:217-229, 1995.

Puliafito, C., M. Hee, J. Schuman & J. Fujimoto, "Optical coherence tomography of ocular diseases," Ch. 1, 2 & Appendix, (Slack, Inc., Thorofare, NJ), 1995.

Sansdrap, P. & A. Moës, "Influence of manufacturing parameters on the size characteristics and the release profiles of nifedipine from poly(DL-lactide-co-glycolide) microspheres," *Int. J. Pharm.*, 98:157-164, 1993.

Schmitt, J., A. Knüttel & R. Bonner, "Measurements of optical properties of biological tissues by low-coherence reflectometry," *Appl. Optics*, 32:6032-6042, 1993.

Schmitt, J., A. Knüttel, M. Yadlowsky & M. Eckhaus, "Optical-coherence tomography of a dense tissue: statistics of attenuation and backscattering," *Phys. Med. Biol.*, 39:1705-1720, 1994.

Schmitt, J., M. Yadlowsky & R. Bonner, "Subsurface imaging of living skin with optical coherence microscopy," *Dermatology*, 191:93-98, 1995.

Sergeev, A., V. Gelikonov, G. Gelikonov, F. Feldchtein, R. Kuranov, N. Gladkova, N. Shakhova, L. Snopova, A. Shakhov, I. Kuznetzova, A. Denisenko, V. Pochinko, Y. Chumakov & O. Streltzova, "*In vivo* endoscopic OCT imaging of precancer and cancer states of human mucosa," *Optics Express*, 1:432-440, 1997.

Shiga, K., N. Muramatsu & T. Kondo, "Preparation of Poly(D,L-lactide) and Copoly(lactide-glycolide) Microspheres of Uniform Size," *J. Pharm. Pharmacol.*, 48:891-895, 1996.

Sivak Jr., M., K. Kobayashi, J. Izatt, A. Rollins, R. Ung-runyawee, A. Chak, R. Wong, G. Isenberg & J. Willis, "High-resolution endoscopic imaging of the GI tract using optical coherence tomography," *Gastrointest. Endosc.*, 51:474-479, 2000.

Su, M., A. Mühler, X. Lao, and O. Nalcioglu, "Tumor characterization with dynamic contrast-enhanced MRI using MR contrast agents of various molecular weights," *Magn. Reson. Med.*, 39:259-269 (1998).

Suslick, K. & E. Flint, "Versatile sonochemical reaction vessels" in *Experimental Organometallic Chemistry: A Practicum in Synthesis and Characterization*, (A. Wayda, Darensburg MY, eds. ACS Symposium Series, Washington, D.C.) 185, 1987.

Suslick K., "Sonochemistry," *Science*, 247: 1439-1445, 1990.

Suslick, K. & M. Grinstaff, "Protein Microencapsulation of Nonaqueous Liquids," *J. Am. Chem. Soc.*, 112:7807-7809, 1990.

Tearney, G. B. Bouma, S. Boppart, B. Golubovic, E. Swanson & J. Fujimoto, Rapid acquisition of *in vivo* biological images by use of optical coherence tomography, *Optics Letters*, 21:1408-1410, 1996.

Tearney, G., S. Boppart, B. Bouma, M. Brezinski, N. Weissman, J. Southern & J. Fujimoto, "Scanning single-mode fiber optic catheter-endoscope for optical coherence tomography," *Optics Letters*, 21:543-545, 1996.

Tearney, G., M. Brezinski, S. Boppart, B. Bouma, N. Weissman, J. Southern, E. Swanson & J. Fujimoto, "Catheter-based optical imaging of a human coronary artery," *Circulation*, 94:3013, 1996.

Tearney, G., M. Berzinski, B. Bouma, S. Boppart, C. Pitris, J. Southern & J. Fujimoto, "*In vivo* endoscopic optical biopsy with optical coherence tomography," *Science*, 276:2037-2039, 1997.

Tearney, G., M. Brezinski, J. Southern, B. Bouma, S. Boppart & J. Fujimoto, "Optical Biopsy in Human Gastrointestinal Tissue Using Optical Coherence Tomography," *Am. J. Gastroenterol.*, 92:1800-1804, 1997.

Tearney, G., M. Brezinski, J. Southern , B. Bouma, S. Boppart & J. Fujimoto, "Optical Biopsy in Human Urologic Tissue Using Optical Coherence Tomography," *J. Urol.*, 157:1915-1919, 1997.

Toublan, F., K. Suslick, J. Reynolds, S. Hartleben, S. Sitafalwalla & S. Boppart, "Magnetically-inducible optical contrast agents for optical coherence tomography." Optical Society of America Biomedical Topical Meeting, Apr. 7-10, 2002, Miami, FL.

Turkevich, J., P. Stevenson & J. Hillier, "A study of the nucleation and growth processes in the synthesis of colloidal gold," *Discuss. Faraday Soc.*, 11:55-75, 1951.

van der Laan, B., G. Jansen, G. Kathmann, G. Westerhof, J. Schornagel & G. Hordijk, "*In vitro* activity of novel antifolates against human squamous carcinoma cell lines of the head and neck with inherent resistance to methotrexate," *Int. J. Cancer*, 51:909-914, 1992.

Violante MR & P.B. Dean. "Improved detectability of VX2 carcinoma in the rabbit liver with contrast enhancement in computed tomography," *Radiology*, 134:237-239 (1980).

Wang, D., A. Rogach & F. Caruso, "Semiconductor quantum dot-labeled microsphere bioconjugates prepared by stepwise self-assembly," *Nano Lett.*, 2:857-861, 2002.

Webb, A., M. Wong, K. Kolbeck, R. Magin, & K. Suslick, "Sonochemically produced fluorocarbon microspheres: a new class of magnetic resonance imaging agent," *J. Mag. Res. Imaging*, 6:675-683, 1996.

Wong, M. & K. Suslick, "Sonochemically produced hemoglobin microbubbles," *Mat. Res. Soc. Symp. Proc.*, 372:89-94, 1995.

Yazdanfar, S., I. Kulkarni & J. Izatt, "High resolution imaging of *in vivo* cardiac dynamics using color doppler optical coherence tomography," *Optics Express*, 1:424-431, 1997.

F. Toublan, et al., "Magnetically-inducible optical contrast agents for optical coherence tomography", presented at the Optical Society of America Biomedical Topical Meeting, Miami, FL, Apr. 7-10, 2002.

\* cited by examiner

Negatively Charged Microspheres → Positively Charged Material → Negatively Charged Material

OPTICAL CONTRAST AGENTS FOR OPTICALLY MODIFYING INCIDENT RADIATION

FEDERALLY SPONSORED RESEARCH OR DEVELOPMENT

The subject matter of this application may in part have been funded by the National Science Foundation (BES-0086696). The government may have certain rights in this invention.

BACKGROUND

When imaging biological tissues, it is often desirable to enhance the signals measured from specific structures. Contrast agents, which produce a strong emission or reflection signal, have been utilized in virtually every imaging modality including ultrasound [2], computed tomography [57], magnetic resonance imaging [58], and optical microscopy [59].

Optical coherence tomography (OCT) is an emerging high-resolution medical and biological imaging technology [15–21]. OCT is analogous to ultrasound B-mode imaging except reflections of low-coherence light are detected rather than sound. OCT detects changes in the backscattered amplitude and phase of light.

Cross-sectional OCT imaging is performed by measuring the backscattered intensity of light from structures in tissue. This imaging technique is attractive for medical imaging because it permits the imaging of tissue microstructure in situ, yielding micron-scale imaging resolution without the need for excision and histological processing. Because OCT performs imaging using light, it has a one- to two-order-of-magnitude higher spatial resolution than ultrasound and does not require contact with tissue.

OCT was originally developed and demonstrated in ophthalmology for high-resolution tomographic imaging of the retina and anterior eye [22–24]. Because the eye is transparent and is easily optically accessible, it is well-suited for diagnostic OCT imaging. OCT is promising for the diagnosis of retinal disease because it can provide images of retinal pathology with 10 μm resolution, almost one order-of-magnitude higher than previously possible using ultrasound. Clinical studies have been performed to assess the application of OCT for a number of macular diseases [23,24]. OCT is especially promising for the diagnosis and monitoring of glaucoma and macular edema associated with diabetic retinopathy because it permits the quantitative measurement of changes in the retinal or retinal nerve fiber layer thickness. Because morphological changes often occur before the onset of physical symptoms, OCT can provide a powerful approach for the early detection of these diseases.

Recently, OCT has been applied for imaging a wide range of nontransparent tissues [16,17,25–27]. In tissues other than the eye, the imaging depth is limited by optical attenuation due to scattering and absorption. A "biological window" exists in tissue where absorption of near-infrared wavelengths is at a minimum and light can penetrate deep into highly-scattering tissue (FIG. 3) [28]. Because optical scattering decreases with increasing wavelength, OCT in nontransparent tissues has routinely used 1.3 μm wavelength light for imaging. In most tissues, imaging depths of 2–3 mm can be achieved using a system detection sensitivity of 110 dB (1 part in $10^{11}$). OCT has been applied to image arterial pathology in vitro and has been shown to differentiate plaque morphology with superior resolution to ultrasound [17,29].

Imaging studies have also been performed to investigate applications in gastroenterology, urology, and neurosurgery [30–32]. High resolution OCT using short coherence length, short-pulse light sources, has also been demonstrated and axial resolutions of less than 5 μm have been achieved [33,34]. High-speed OCT at image acquisition rates of 4 to 8 frames per second for 500 to 250 square pixel images has been achieved [35]. OCT has been extended to perform Doppler imaging of blood flow and birefringence imaging to investigate laser intervention [36–38]. Different imaging delivery systems including transverse imaging catheters and endoscopes, and forward imaging devices have been developed to enable internal body OCT imaging [39,40]. Most recently, OCT has been combined with catheter-endoscope-based delivery to perform in vivo imaging in animal models and human patients [41–44].

Apart from medical applications, OCT has been demonstrated as an emerging investigational tool for cell and developmental biology. OCT has imaged the development of numerous animal models including *Rana pipiens* and *Xenopus laevis* (Leopard and African frog), and *Brachydanio rerio* (zebrafish) [45–46]. High-speed OCT imaging has permitted the morphological and functional imaging of the developing *Xenopus* cardiovascular system, including changes in heart function following pharmacological interventions [47]. High-resolution imaging has permitted the real-time tracking of cell dynamics in living specimens including mesenchymal cell mitosis and neural crest cell migration [48]. OCT is advantageous in microscopy applications because repeated non-invasive imaging of the morphological and functional changes in genetically modified animals can be performed overtime without having to histologically process multiple specimens. The high-resolution, cellular-imaging capabilities suggest that OCT can be used to diagnose and monitor early neoplastic changes in humans.

The ability of OCT to perform optical biopsies, the in situ imaging of tissue microstructure at near-histological resolution, has been used to image morphological differences between normal and neoplastic tissue. OCT images of in vitro neoplasms of the female reproductive tract [49], the gastrointestinal tract [50], and the brain [51] have been investigated. Optical differences between normal and neoplastic tissue were evident, but primarily for late-stage changes. Still, situations exists where no inherent optical contrast exists between normal and pathologic tissue, such as in early-stage, pre-malignant tumors or in tumors which remain optically similar to normal tissue.

In the past, OCT has found numerous medical and biological applications. However, the imaging technique has relied largely on the inherent optical properties of the tissue to provide contrast and differentiate normal from pathological tissue. Phospholipid-coated perfluorobutane microbubbles (ImaRx Pharmaceutical, Tucson, Ariz.) have been used as a contrast agent for OCT; although they produce a strong OCT signal, blood and tissue also produce a fairly strong OCT signal, and the effects of this contrast agent in vivo on the visualization of blood vessels are subtle [60].

Albunex® is an FDA-approved, air-filled albumin composed of microparticles produced ultrasonically, that is used intravenously as an echo-contrast agent for echocardiography, and as a contrast agent for ultrasound imaging [2–4]. These microparticles may be formed with encapsulated liquid, to form a unique colloidal delivery vehicle. By the choice of protein used for the microparticle shell, the material encapsulated within the microparticle, a multitude of biomedical applications have been developed [3,5–9]. Some of the applications of these protein microparticles include biocompatible blood substitutes, magnetic resonance imaging and echocardiographic contrast agents, and novel drug delivery systems. These are described in the following U.S. Pat. Nos. 5,362,478; 5,439,686; 5,498,421; 5,505,932; 5,508,021; 5,512,268; 5,560,933; 5,635,207; 5,639,473; 5,650,156; 5,665,382 and 5,665,383.

These protein microparticles may be created from ultrasonic irradiation of aqueous protein solutions. Studies have delineated that the mechanism responsible for microparticle formation is, in fact, a combination of two acoustic phenomena: emulsification and cavitation. Ultrasonic emulsification creates the microscopic dispersion of the protein solution necessary to form the proteinaceous microparticles. Alone, however, emulsification is insufficient to produce long-lived microparticles. For example, emulsions produced by vortex mixing produce no long-lived microparticles.

Ultrasonic irradiation of liquids can also produce cavitation, the formation, growth, and implosive collapse of bubbles. The collapse of such bubbles creates transient hot-spots with enormous peak temperatures [14]. Sonolysis of water is known to produce $H^+$, $OH^-$, $H_2$, $H_2O_2$, and in the presence of oxygen, $HO_2$ [13]. Superoxide creates interprotein disulfide bonds that cross-link the proteins and hold the microparticles together. This dispersion of gas or non-aqueous liquid into the protein solution, coupled with chemical cross-linking of the protein at the microparticle interface results in the formation of long-lived microparticles filled with air or nonaqueous liquid.

BRIEF SUMMARY

In a first aspect, the present invention is a method of forming an image of a sample, comprising forming an image of a mixture, by exposing the mixture to electromagnetic radiation. The mixture comprises the sample and microparticles.

In a second aspect, the present invention is a method of enhancing the contrast of an image of a sample, comprising forming an image of a mixture, by exposing the mixture to electromagnetic radiation. The mixture comprises the sample and microparticles.

In a third aspect, the present invention is a method of forming an image by optical coherence tomography, including exposing a patient to electromagnetic radiation, collecting reflected electromagnetic radiation, and forming an image from the collected electromagnetic radiation, the improvement comprising administering a contrast agent to the patient to enhance contrast of the image.

DETAILED DESCRIPTION

The present invention makes use of the discovery that microparticles may be used to enhance the contrast in analyses and imaging techniques that use electromagnetic radiation, particularly those techniques which use radiation in the frequency range of infra-red to ultraviolet, such as OCT, light microscopy, holography, confocal microscopy, multi-photon microscopy, and endoscopy.

The phrase "enhancing the contrast" means that an image produced with the enhancement shows a greater difference in adsorbed, scattered or reflected electromagnetic radiation between parts of the image, than an otherwise identical image produced without the enhancement.

The term "image" means data produced by receipt of electromagnetic radiation, which may or may not be formed into a picture viewable by the human eye. This includes images produced directly onto a medium such as film or video.

The phrase "frequency range of infra-red to ultraviolet" means electromagnetic radiation having a frequency of $10^{12}$ to $10^{17}$ Hz, which excludes radio waves, microwaves, X-rays and gamma rays. The term "light" means visible light.

Microparticles have a solid component, such as an outer shell, and may have an inner core which is gas, liquid or solid (which may be the same or different from the outer shell). Preferably, the microparticles have an outer shell containing biodegradable polymers. More preferably, the microparticles have an outer shell containing cross-linked protein.

The term "solid" includes cross-linked proteins; cross-linked polymers; and materials which exhibit a melting point $(T_m)$ or a glass transition temperature $(T_g)$ in differential scanning calorimetry (DSC) which is above 30° C., more preferably above 50° C., most preferably above 100° C.

Preferably, the microparticles have an average diameter of at least 100 nm, more preferably at least 0.5 microns, even more preferably 0.5–15 microns, most preferably 0.5–5 microns. Preferably, the microparticles have an average diameter of at most 50 microns, more preferably 100 nm to 50 microns. As used herein, the term "diameter" and "average diameter", in the context of microparticles, means number average diameter.

Varying the microparticle diameter enables size-selectivity for use in the living microcirculation or for optimizing the wavelength-specific scattering properties of the contrast agents. When the microparticle size is on the same scale as the wavelength of the incident radiation, Mie scattering predicts the behavior of the scattered light and can be used to maximize scattering for particular wavelengths.

Figure 8:
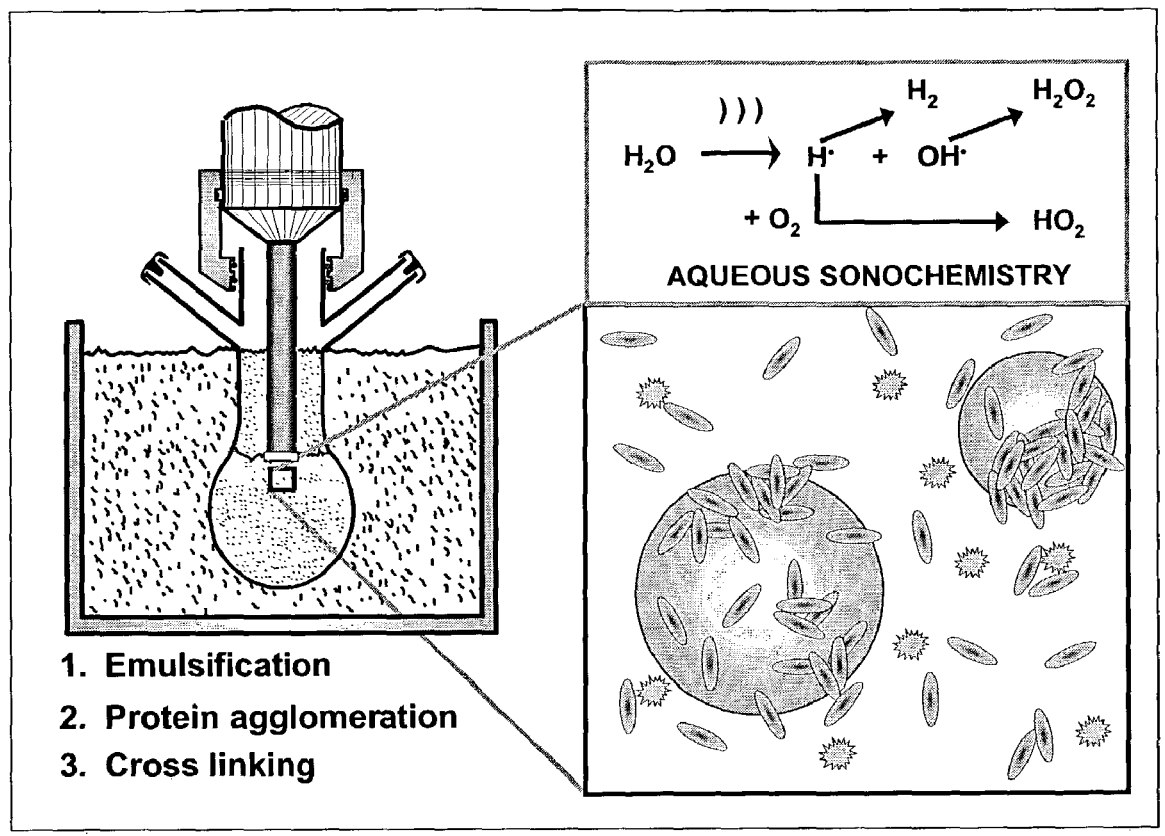
FIG. 8 is an illustration of the step for forming microparticles.

Any protein may be used in the microparticles. The term "protein" includes proteins, peptides and polypeptides, both natural and synthetic. In the fabrication of protein microparticle, there are three main steps: emulsification, protein agglomeration, cross-linking. The first two steps are a result of the mixing effect caused by ultrasound. The third step is a result of the sonolysis of water. When exposed to high intensity ultrasound (20 kHz), water molecules are split into highly reactive intermediates. Superoxide, which is produced during the sonolysis of water, cross-links the protein molecules. The cross-linking of the microparticles is done via the oxidation of the cysteine residues to form inter-protein disulfide bonds. The general process is depicted in FIG. 8. Using this particular set-up, a variety of microparticles have been produced. The material to be encapsulated should be dissolved into a two-phase system comprising an aqueous phase and an oil phase during the emulsification. In addition to liquids, solids and gasses can also be encapsulated inside the microparticle. For example air has been encapsulated in protein microparticles. This product Albunex™ is commercially available as an echo contrast agent.

During the formation of the microparticles, cysteine residues are reacted, forming disulfide bonds that cross-link the protein. If the protein does not contain cysteine residues, the protein may be modified with 2-iminothiolane (Traut's reagent) using the chemical scheme shown below.

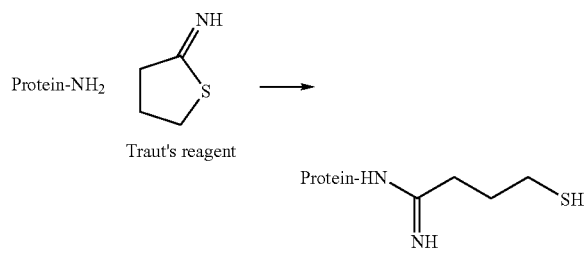

Once modified, any protein can be used for microparticle synthesis. The more thiol groups introduced, the greater the microparticle yield and stability. This is consistent with the fact that cross-linking is done via inter-protein disulfide bond formation.

Preferably, the polymers for use with the present invention are materials which decompose when placed inside an organism. This can be observed as a decline in the molecular weight of the polymer over time. Polymer molecular weights can be determined by a variety of methods including size exclusion chromatography (SEC), and are generally expressed as weight averages or number averages. A polymer is biodegradable if, when in phosphate buffered saline (PBS) of pH 7.4 and a temperature of 37° C., its weight-average molecular weight is reduced by at least 25% over a period of 6 months as measured by SEC.

Examples of biodegradable polymers include proteins, polyesters, such as poly(ε-caprolactone), poly(glycolic acid), poly(L-lactic acid), poly(D-lactic acid), poly(hydroxybutyrate) and copolymers of caprolactone, glycolic acid, lactic acid, and hydroxybutyrate; polyanhydrides, such as poly(adipic anhydride); poly(paradioxanone); poly(β-malic acid); polyethylene glycol; polyamines; polyurethanes; polyesteramides; polyorthoesters; polyacetals; polyketals; polycarbonates; polyorthocarbonates; polyphosphazenes; poly(malic acid); poly(amino acids); polyvinylpyrrolidone; polyhydroxycellulose; chitin; chitosan; and copolymers and mixtures thereof.

Any biodegradable polymer may be used to fabricate the shell of microparticles. Preferably, biodegradable polymers that contain sulfhydryl functionality may be used to fabricate microparticles, as sonolysis will yield interpolymer disulfide bonds between adjacent polymers. Biodegradable polymers that contain reactive groups other than sulfhydryl groups, such as amine groups, can be modified initially with Traut's reagent as described previously to introduce the requisite sulfhydryl functionality for fabricating the cross-linked polymer shell of microparticles using sonolysis. Even more preferably, biodegradable polymers that contain multiple functionalities, such as amino, carboxylate, ester, hydroxyl, and sulfhydryl functionalities, would enable fabrication of microparticles having cross-linked polymer shells that may be subject to further surface modification.

The biodegradable polymers that make up the polymer shell of microparticles need not be homopolymers nor uniform mixtures of a given polymer. Biodegradable homopolymers, heteropolymers, or mixtures thereof may be used in microparticle fabrication protocols, provided the polymers possess sulfhydryl functionality necessary for formation of microparticle having a cross-linked biodegradable polymer shell. Such polymers are commercially available or may be prepared using methods routinely available to one of ordinary skill in the art.

One or more materials may be encapsulated in each microparticle. Changes in the inner core allows for versatility of the microparticles in biomedical applications. Table 1 lists some of the types of microparticles that have been synthesized. In addition to the inner core materials in the list, melanin granules, colloidal gold, iron oxide, and fluorophores, all of which have the potential to absorb, scatter, spectrally-modify, or modulate the incident radiation, may be used. Still other examples include liquid crystalline materials, biocompatible liquid crystals in the cholesterol family such as cholesterol oleyl carbonate, fatty alcohol esters of tartaric acid and cholesteryl oligo(L-lactic acids), chiral agents such as helocenes, tartaric acid and esters thereof, other optically active organic compounds, and birefringent materials, which may be used in conjunction with planar or circularly polarized light. Dye and pigments may also be included, such as porphyrins, metalloporphyrins, nile red, rhodamine, and phthalocyanines. Preferably, the microparticle are optically dense; the term "optically dense" means that the microparticles absorbs at least twice as much visible light than an equivalent thickness of water-filled microparticles formed from bovine serum albumin. For X-ray application, preferably the microparticles are X-ray dense; the term "X-ray dense" means that the microparticles absorb at least twice as much $Cu_{K\alpha}$ X-ray radiation, than an equivalent thickness of water-filled microparticles formed from bovine serum albumin.

TABLE 1

| Microparticles | | |
|---|---|---|
| Protein Shells | Inner Cores | Surface Coats |
| Albumin | Air, $O_2$, $N_2$, Ar | PEG |
| Hemoglobin | Vegetable oil | Fluorescein |
| Pepsin | Water | Iron oxide colloid |
| Immunoglobulins | Organic liquids | Immunoglobulins |
| Lipase | Acetoacetate | Folate |
| Peroxidases | Fluorocarbons | Gd complexes |
| Modified Myoglobin | Iodinated agents | Monoclonal Antibodies |
| Gold Labeled Albumin | Gd complexes | Gold nanoparticles |
| | Iron Oxide | Silica nanoparticles |
| | | Melanin |
| | | Carbon |

Figure 9:
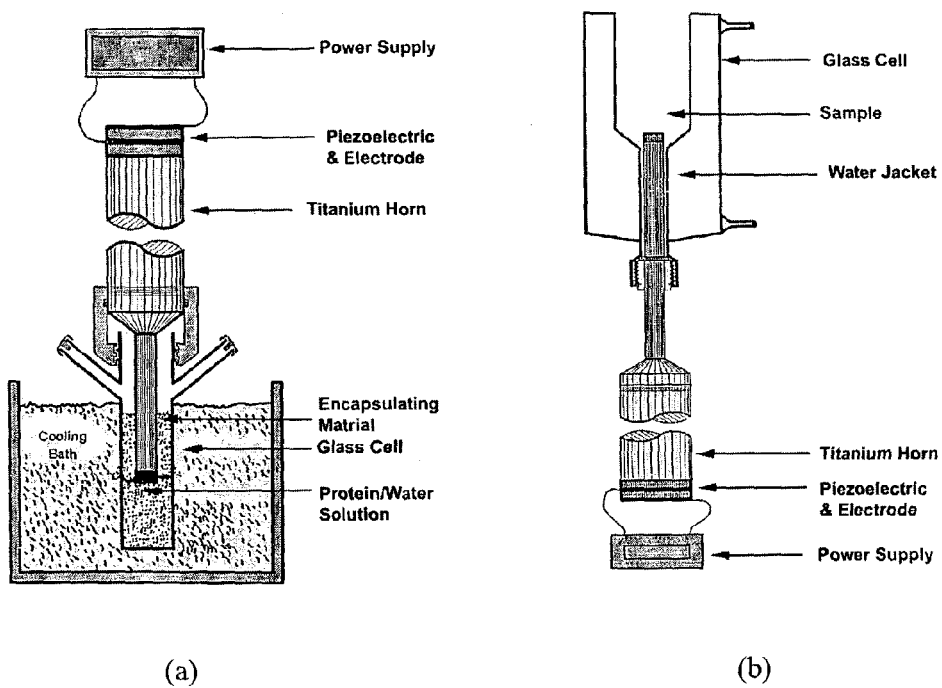
FIGS. 9(a) and (b) are diagrams of the standard cell and inverted cell, respectively, for forming microparticles.

Hydrophilic materials and charged material can be introduced in the microparticles using a modification of the cell employed (inverted cell as opposed to the standard cell). Diagrams of the standard cell (left), as well as one of the inverted cell (right) are shown in FIG. 9.

Two or more different materials may be encapsulated in each microparticle to provide high or low contrast under different conditions, such as in an applied alternating field. As an example, one or more of the encapsulated material is either charged (for electrically-modulated agents) or magnetic (for magnetically-modulated agents). These agents may be responsible for either low or high contrast. The second type of material to be encapsulated is intended to provide the opposite contrast of the first such as titanium oxide, or may be a bulk material such as oil, or both. Examples of charged agents include Reichardt's dye (RD; a solvatochromic agent) and 1-ethyl-4-methoxycarbonyl) pyridinium iodide (PYI), the structures of which are shown below. Examples of magnetic agents include iron particles, iron oxide, ferrox cube A, alnico 8, cunife, cunico, iron particles coated titanium oxide (formed by sputtering the iron particles with titanium oxide), and cobalt particles coated with gold (formed by plating of gold onto cobalt particles).

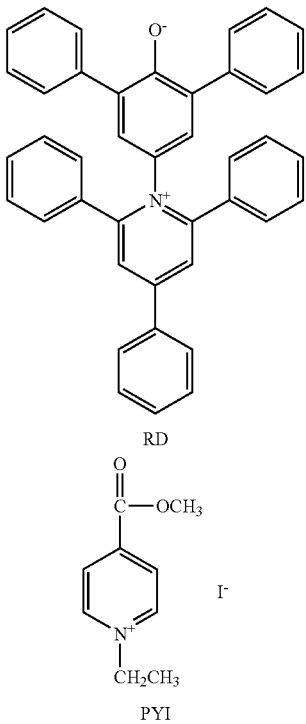

Previously, microparticles have been examined by optical microscopy, scanning and transmission electron microscopy, and particle counting. The microparticles have a uniform size distribution with diameters of roughly 2 μm, permitting unimpeded motion throughout the circulatory system. While the protein shells may be quite thin (roughly 50 angstroms across) and gas permeable, the particles are physically robust and will survive filtration and centrifugation. Their synthesis produces very large concentrations (>$10^{10}$ microparticles/mL after purification).

Sonochemical methods that use high-intensity ultrasound and simple protein solutions may be used to make both air-filled microparticles and liquid and particle-filled microcapsules [5]. For example, a 1–15% weight per volume solution of protein in water may be mixed with the liquid or the particles to be encapsulated. High intensity 20 kHz ultrasound may be applied at the interface of the materials for 1–10 minutes at an acoustic power of 30–150 watts/cm². Temperature should be controlled by a water bath. Microparticles may be washed multiple times by centrifuge filtration, for example at 3 g for 20 minutes. The microparticle-containing layer may then be separated and remaining layers discarded. Contrast agents that can have their contrast modulated by external electric or magnetic fields are fabricated in a similar manner, except, two or more different materials are encapsulated in each microparticle. Microparticle diameter can be controlled by varying the acoustic power of the ultrasound wave. This sonochemical technique produces micron-sized particles with a cross-linked protein shell and a core which may be selected freely.

Native protein and extensively purified protein microparticles show very similar spectra. Formation of microparticles does not significantly alter the secondary structure of the protein that makes up the cross-linked shell.

The surface of the microparticles can be altered to vary the in vivo pharmacokinetics and biodistribution. Towards this goal, attached molecules include, but are not limited to, polyethylene glycol chains (PEG) (to extend their lifetime in the blood pool), membrane receptor ligands (e.g., folate, hemes, steroids, neurotransmitters), bioactive peptides, and even antibody chains. Furthermore, lipase can be attached to the surface of the microparticles to preferentially target the small intestines.

The availability of numerous functionalizable side groups in proteins makes it easier to modify the surface of microparticles with shell compositions made from cross-linked protein. Modification of protein microparticles allows for prolonged circulation in the case of polyethylene glycol (PEG) attachment, surface recognition in the case of folate and antibody attachment, and changes in optical and spectroscopic properties in the case of colloids adhesion. Five different surface modification routes are described here.

Covalent attachment of polyethylene glycol (PEG) to the amine group on the protein microparticle. These residues can be modified to introduce functionality such as the polyethylene glycol (PEG) group. The introduction of the PEG group is done via a coupling reaction with cyanuric chloride. The reaction scheme is shown below.

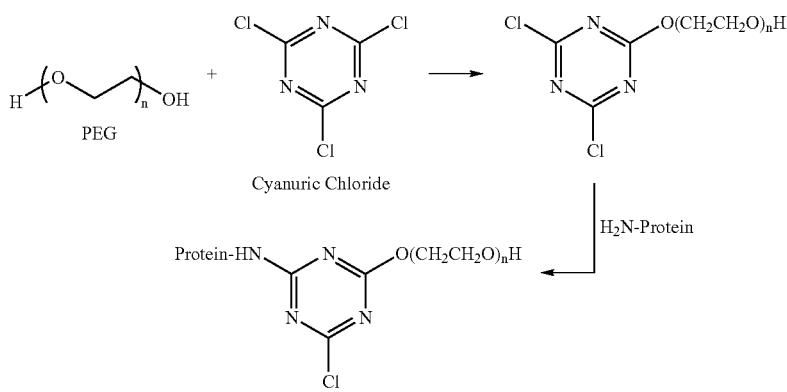

Surface modification using folate is an extension of the PEG surface modification method shown above. The folate in this instance is activated using a dicyclohexyl carbodiimide (DCC) coupling reaction. The activated folate is then coupled to a PEG moiety. This process is depicted below. The resulting modified PEG is attached to the surface of the microparticles in the same manner as depicted above via a cyanuric chloride coupling reaction.

breast, and human nasopharyngeal tumors all possess a high concentration of folate receptors on their surface [52,53]. Prior work has shown that liposomes modified by folate-PEG conjugates target folate receptor bearing KB tumor cells and exhibit an inhibitory effect on their growth [54]. Specifically, these contrast agents are expected to target induced squamous cell carcinoma with the folate-modified microparticles. Similarly, many oral and upper gastrointes-

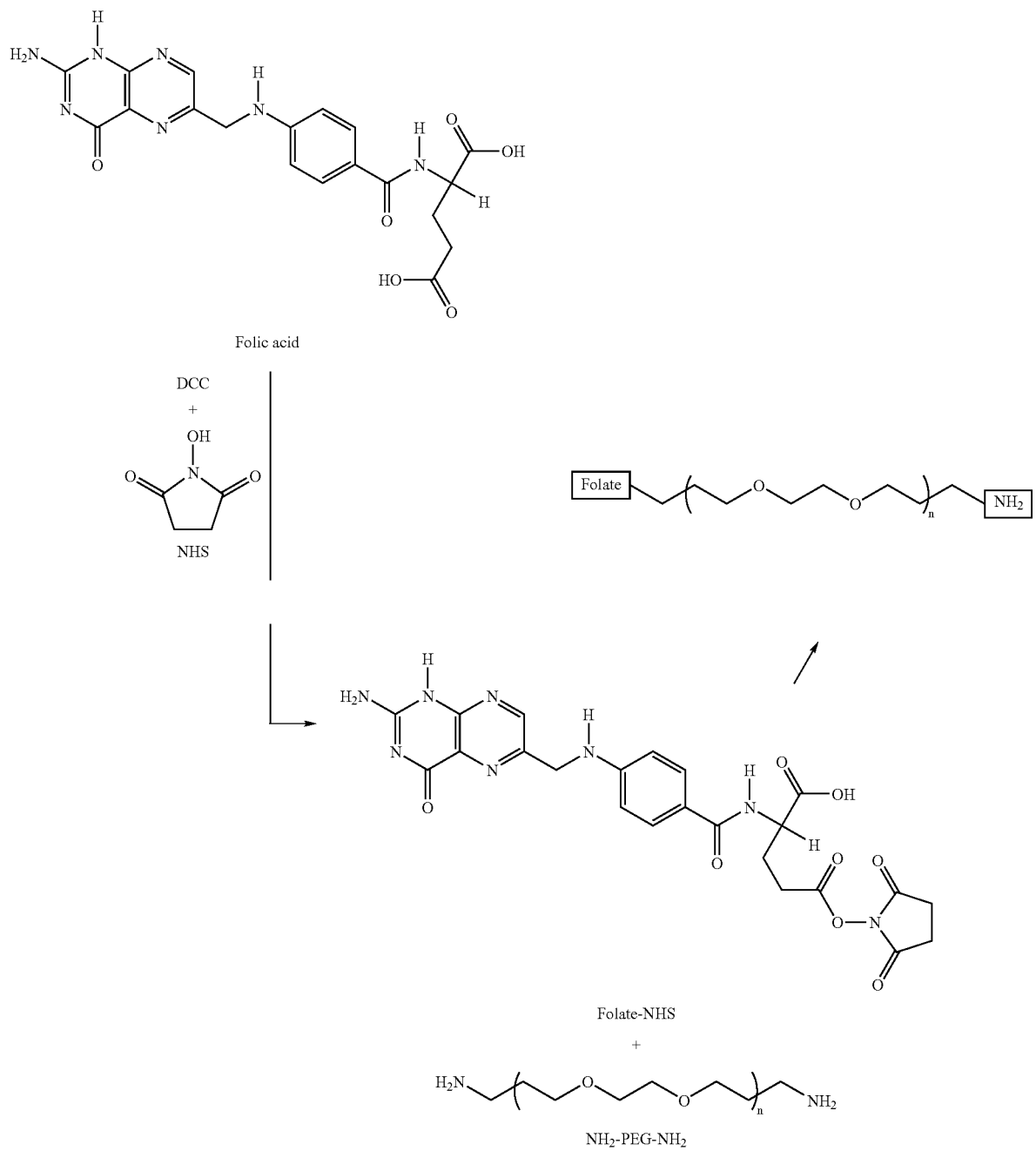

The conjugation of folate to the microparticle surface allows targeting to folate-binding tumor cells. Ovarian, tinal tract tumors have a high affinity for various hemes (which greatly assists in the use of hematoporphyrins as photodynamic therapy agents) [55,56]. Microparticles with surface hemes attached may also be used to target induced squamous cell carcinoma.

The modification of the protein microparticles with antibodies allows targeting of T-cell receptors. This modification was carried out using monoclonal antibodies that are specific for T-cell receptors. These monoclonal antibodies were covalently linked to the surface of the microparticles via a dimethylaminoprol-carbodiimide hydrochloride (EDC) coupling reaction. In this coupling reaction the glutamates (residues which contain carboxylates groups) and the lysines (residues which contain primary amine groups) of both the antibodies and the protein microparticles are cross-linked. The general scheme of this process is shown below. This may be used to form a surface coat of any protein which contains glutamate and lysine residues.

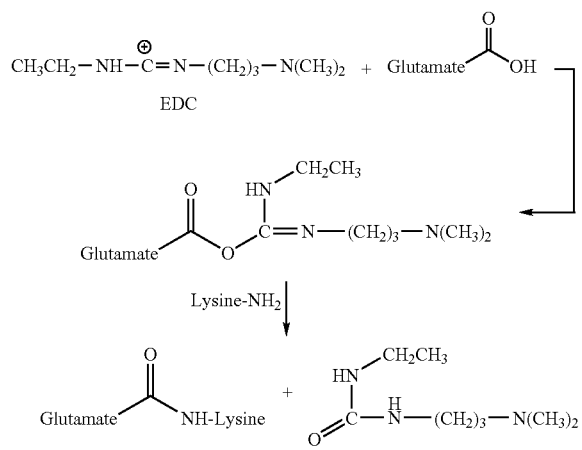

Figure 10:
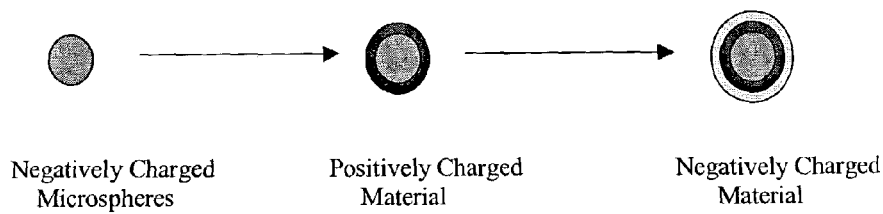
FIG. 10 depicts a method of coating colloidal suspensions onto microparticles.

Modifications using aqueous colloidal suspension relies on the surface charge of the microparticles for particulate adhesion. This method has been employed in the thin film industry to place charged particles onto a template. A microparticle having a negative charge, for example one formed from BSA and kept at a pH of 7.4, is formed and positively charged material may be adhered onto the surface following a layer-by-layer approach, by simply mixing it with the colloidal material. This method is depicted in FIG. 10.

Other materials may be put on the surface by following the usual microparticle synthesis route but by using a non-colloid suspension of the desired material in the oil phase. Because the oil does not appropriately solvate the suspended particles, upon microparticle formation these particles preferentially attach to the exterior of the protein shell to avoid contact with the oil phase. Examples of these microparticles are the melanin and carbon surface coat containing microparticles.

The protein shell of serum albumin microparticles with a n-$C_9F_{20}$ core can be modified. In rats, the measured circulation half-life of non-modified microparticles was approximately 5 minutes, while surface modification with PEG extends this to more than 70 minutes.

These and other techniques for preparing the contrast agents are described in U.S. patent application Ser. No. 10/463,833, entitled "SURFACE MODIFIED PROTEIN MICROPARTICLES", to Kenneth S. Suslick et al., Attorney docket number 09800240-0035, filed on the same day as this application, the contents of which are hereby incorporated by reference. Still other techniques for preparing these contrast agents are described in U.S. patent application Ser. No. 09/931,640, entitled "MICROPARTICLES", to Kye-kyoon Kim et al., filed Aug. 15, 2001, and published May 9, 2002. This latter technique is very suitable for forming microparticles of polymers which do not contain sulfhydryl groups. Furthermore, in the same fashion as with cross-linked protein microparticles, microparticles formed from other polymers may be surface-modified by inclusion of hydroxyl, sulfhydryl, amino, and carboxylate groups.

Sonochemically-generated contrast agents containing any combination of shell and encapsulated material (as shown in Table 1) may be used to increase local contrast within biological and non-biological specimens and samples. Contrast agents can be delivered to the area of interest by a number of techniques including syringe injection interstitially, intravenouly, intermuscularly, subdermally, inter-paratenielly, and interthecally. Other techniques include oral, rectal and topical administration. The surface modifications to the agents enable them to localize to target tissues or cells by means include receptor-mediated adhesion, anti-gen-antibody localization, or phagocytosis (engulfing) or endocytosis (uptake) by target cells.

The microparticles may be prepared as pharmaceutical compositions. Such compositions typically comprise microparticles and a pharmaceutically acceptable carrier. A "pharmaceutically acceptable carrier" includes any and all solvents, dispersion media, coatings, antibacterial and antifungal agents, isotonic and absorption delaying agents, etc., compatible with pharmaceutical administration [61]. Preferred examples of such carriers or diluents include, but are not limited to, water, saline, finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

A pharmaceutical composition is formulated to be compatible with the intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Injection provides a direct and facile route of administration, especially for tissue that is below the skin. Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, CREMO-PHOR EL (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, such as parabens, chlorobutanol, phenol, ascorbic acid, and thimerosal, can control microorganism contamination. Isotonic agents, such as sugars, polyalcohols such as manitol, sorbitol, and sodium chloride can be included in the composition.

Sterile injectable solutions or dispersions can be prepared by incorporating microparticles in an appropriate solvent with one or a combination of ingredients, followed by sterilization. Sterile powders for the preparation of sterile injectable solutions methods of preparation include vacuum drying and freeze-drying that yield a powder and any desired ingredient from a sterile solutions.

Oral compositions generally include an inert diluent or an edible carrier. For the purpose of oral administration, the microparticles can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

For administration by inhalation, the compounds are delivered as an aerosol spray from a nebulizer or a pressurized container that contains a suitable propellant, e.g., a gas such as carbon dioxide.

Systemic administration can also be mucosal or dermal. For mucosal or dermal administration, penetrants that can permeate the target barrier(s) are selected. Mucosal penetrants include, detergents, bile salts, and fusidic acid derivatives. Nasal sprays or suppositories can be used for mucosal administration. For dermal administration, the microparticles are formulated into ointments, salves, gels, or creams. The microparticles can also be prepared in the form of suppositories (e.g., with bases such as cocoa butter and other glycerides) or retention enemas for rectal delivery.

Oral formulations or parenteral compositions in unit dosage form can be created to facilitate administration and dosage uniformity. Unit dosage form refers to physically discrete units suited as single doses for a subject, containing a effective quantity of microparticles in association with a pharmaceutical carrier.

The pharmaceutical compositions can be included in a kit, container, pack, or dispenser together with instructions for administration. When the invention is supplied as a kit, the different components of the composition may be packaged in separate containers and admixed immediately before use. Such packaging of the components separately may permit better long-term storage.

The reagents included in the kits can be supplied in containers of any sort such that the life of the different components are preserved and are not adsorbed or altered by the materials of the container. For example, sealed glass ampules may contain lyophilized luciferase or buffer that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that may be fabricated from similar substances as ampules, and envelopes, that may consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

Once contrast agents have reached their target tissue or cell, they may remain localized and provide contrast either passively or actively. Passive contrast agents may absorb, scatter, or spectrally-modify the incident radiation. Active contrast agents have their contrast modulated by alternating, externally-applied electric or magnetic fields.

Figure 4:
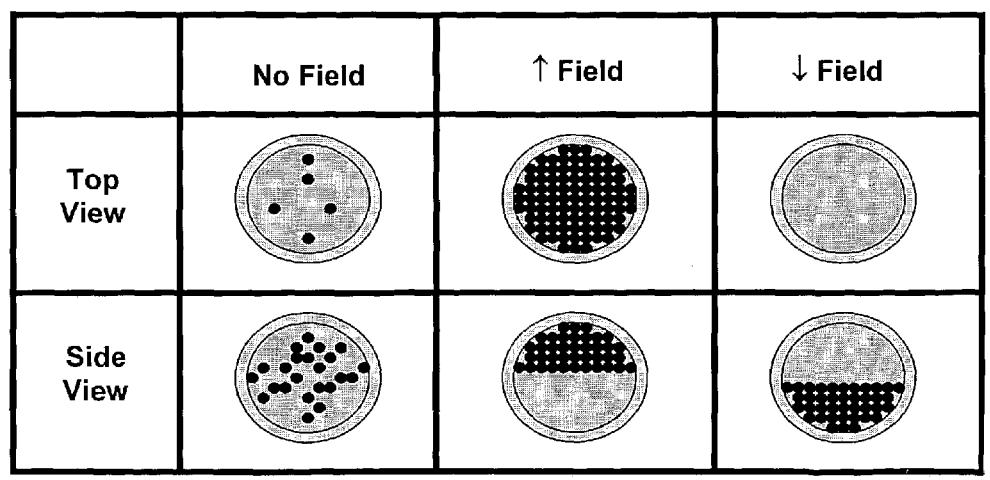
FIG. 4 is a schematic of magnetically- or electrically switchable contrast agents.

Electromagnetic radiation is directed toward the specimen, sample or part of a patient containing the contrast agent. Following interaction with the contrast agent, the affected radiation is detected, typically in either the transmitted (forward) or reflected (backward) directions relative to the direction of the incident radiation. This detected radiation carries information about the specimen, sample or patient, as well as the presence of the contrast agent. This information can be measured and displayed numerically, graphically, or in the form of an image. For active contrast agents that have their contrast modulated by an external field, an alternating electric or magnetic field is applied, inducing an alternating contrast within the agents (FIG. 4). An apparatus for implementing switchable contrast agents would include pairs, series, or arrays of electrodes that would have an electrical potential (dc or ac) and establish an electric field within the specimen to cause the charged particles to be oriented, aligned, or displaced. Magnetic fields may be established using solenoids or coil configurations through which electrical current is passed. Static and alternating magnetic fields and gradients may be used. MRI (Magnetic Resonance Imaging) technology could be leveraged for the use of these contrast agents; the optical imaging could be done within MRI coils. The contrast will modulate at the same frequency as the applied field. Detection with a lock-in amplifier (locked in at the same frequency as the applied field) is used to enhance the sensitivity of the contrast agents. The detection of a signal at the lock-in frequency may be amplified, compared to other signals, thereby enhancing the sensitivity of the detection scheme. Alternatively, moving particles caused by the alternating fields will cause a Doppler-shift in the incident light, and using OCT these frequency shifts would provide a signal that can be detected with high sensitivity, since the background tissue will not be moving.

The lifetime of the contrast agents in living specimens is likely to range from minutes to days, depending on the stability of the agent, the ability of the agent to localize and attach to specific tissue or cells, and the ability of the body to breakdown or clear the agent. Studies of similar agents used in ultrasound and MRI indicate that the agents are cleared rapidly within hours and excretion occurs via both the renal (kidneys) and hepatic (liver) systems. Because of the expected rapid clearance of the agents, side-effects are expected to be minimal.

Figure 5:
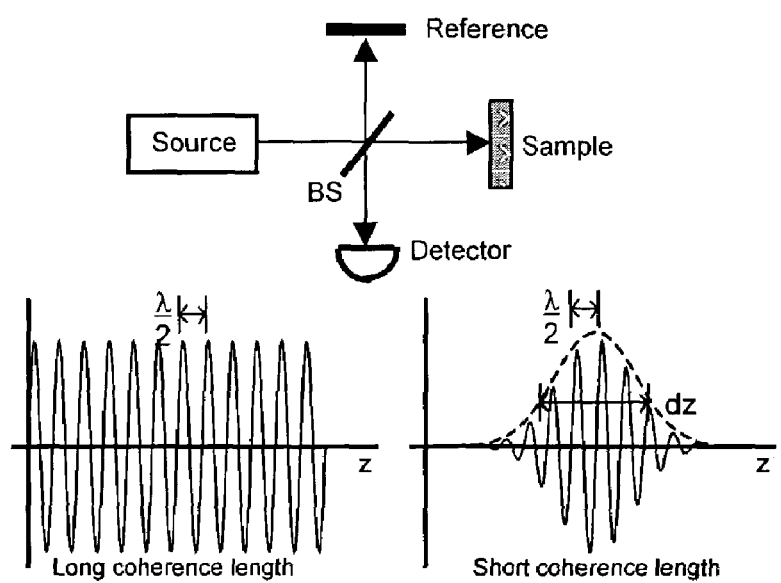
FIG. 5 is a schematic of low-coherence interferometry.
Figure 6:
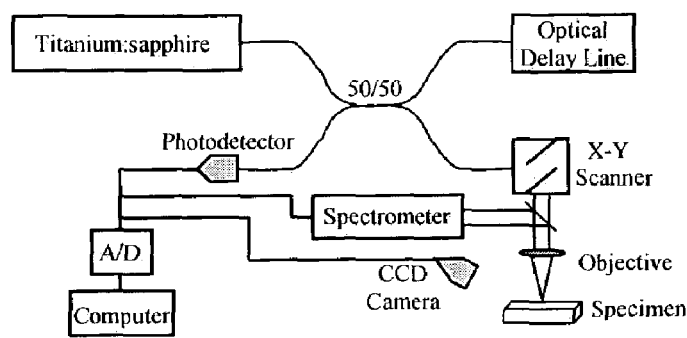
FIG. 6 is a schematic of an OCT instrument.

The contrast agents described here may be used in optical detection and imaging technologies for biological, non-biological, medical, and display applications. OCT is an emerging high-resolution imaging technology that currently lacks contrast agents to enhance its diagnostic capabilities. OCT performs optical ranging and is analogous to ultrasound, except reflections of near-infrared light is detected rather than sound. Because the speed of light is much faster than sound, optical low-coherence interferometry (FIG. 5) must be used to determine the precise location of the optical backscatter. The OCT technology is fiber-optic-based and relies on the rapid technology development of lasers and fiber optics driven by the telecommunications industry. A schematic of the OCT instrument is shown in FIG. 6. The OCT imaging beam can be delivered to internal body locations with the use of fiber-optic probes and catheters. The use of optical contrast agents localized to regions of early cancer will facilitate detection of cancer at early stages, when it is most responsive to treatment.

Figure 7:
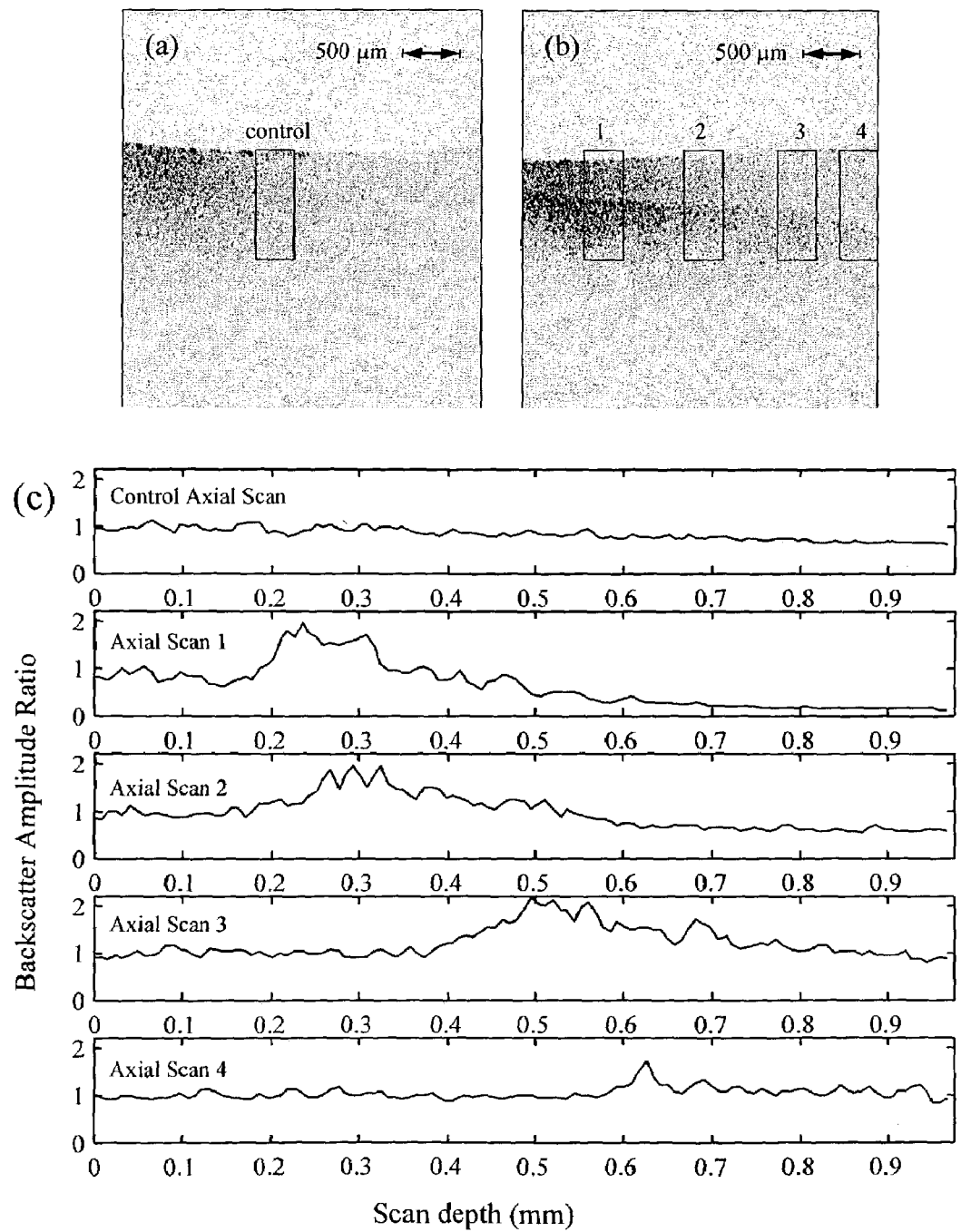
FIGS. 7(a) and (b) are images of air-filled microparticles in a tissue model.
FIG. 7(c) shows plots indicating the degree of optical backscatter versus depth for the boxed areas in FIGS. 7(a) and (b)

FIG. 7 illustrates the use of air-filled microparticles, in a tissue model. Layers of agarose gel mixed with milk to emulate the optical properties of human skin were used to demonstrate how microparticles enhance contrast deep below the surface. A layer of contrast agents can be seen in FIG. 7b. FIG. 7c shows axial plots of data that illustrate the enhancement of contrast up to 650 microns below the surface of the tissue model.

EXAMPLES

The examples herein are illustrations of various embodiments of this invention and are not intended to limit it in any way.

Figure 1:
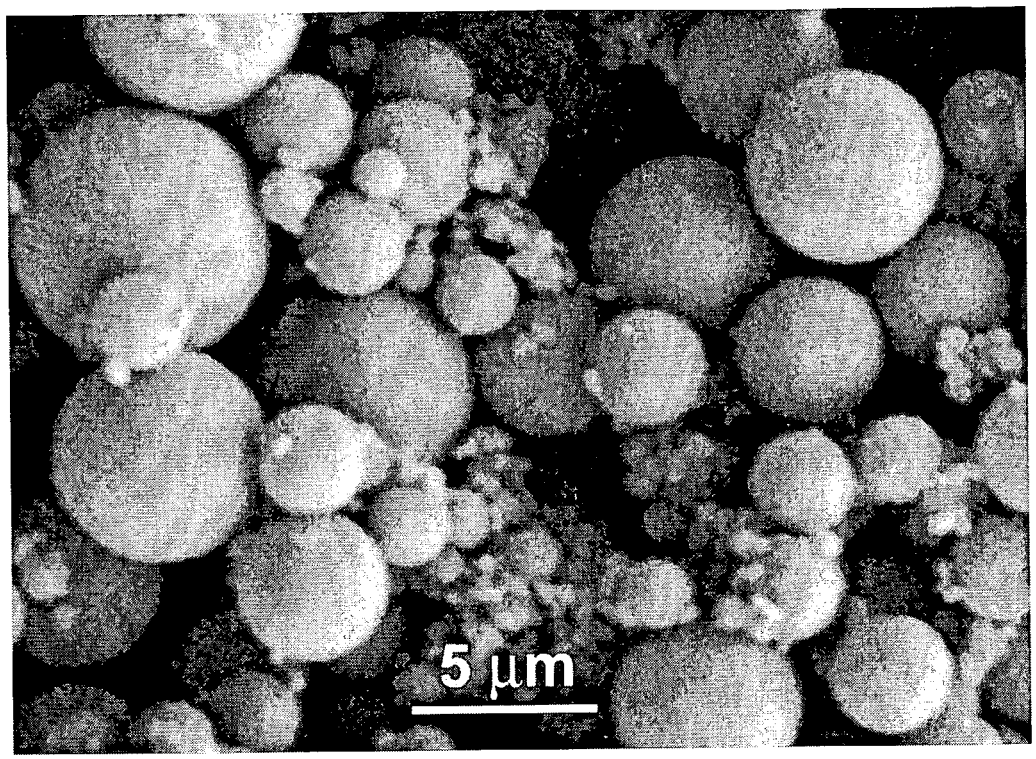
FIG. 1 is a scanning electron microscope image of microparticles.
Figure 2:
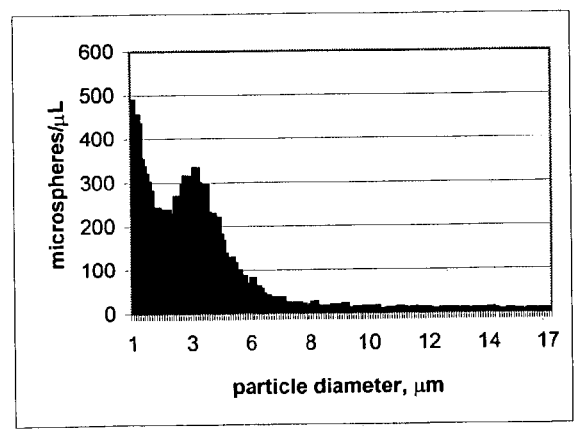
FIG. 2 shows a plot of the distribution of microparticle sizes.
Figure 3:
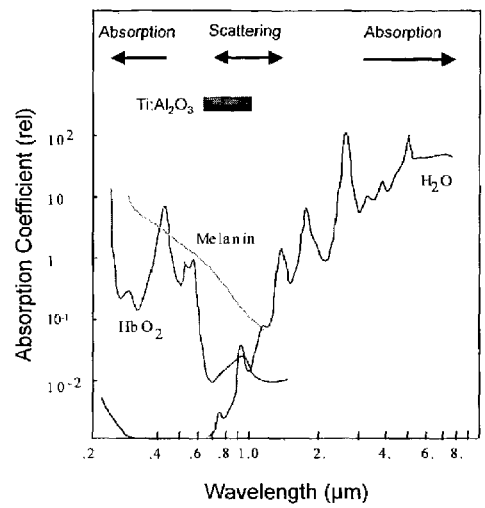
FIG. 3 is a graph of the "biological window" in tissue.

The contrast agents investigated in this study are similar to those used in ultrasound echocardiography [4]. These agents are hollow microparticles 0.5 to 5 microns in diameter with a 50 Å thick protein shell. FIG. 1 shows a scanning electron micrograph of the microparticles. The microparticles utilized were air-filled and produced by sonicating a 5% weight per volume solution of bovine serum albumin (BSA) in water. The high-intensity ultrasound necessary for the reaction was generated by a titanium horn with tip diameter of 0.5 inches, driven at 20 kHz. The BSA solution was sonicated for 3 minutes at an acoustic power of 76 W/cm$^2$ [3]. The microparticles may be re-suspended with 0.1 M 4-morpholine ethane sulfonic acid, pH=4.5. The diameter of the microparticles is dependent on the acoustic power and the frequency of ultrasound used. Diameters ranging from 0.5 microns to 15 microns may be produced with ultrasound. The sample of microparticles was washed 5 times with nanopure water and filtered to remove unwanted particles. FIG. 2 shows a plot of the distribution of microparticle sizes from a 10 µL sample of contrast agents in water. Approximately $1.3 \times 10^5$ microparticles/µL are present within this sample. The distribution plot data was generated from a COULTER® Multisizer II analysis of the sample. The microparticle sizes are generally under 5 microns with an average and standard deviation of 2.2±0.5 µm. This size distribution should enable them to pass readily through the microcirculation. These microparticles can also be filled with other scattering substances such as melanin, gold, or iron particles suspended in oil [5]. The air-filled particles (refractive index n≈1) are expected to scatter strongly in tissue (n≈1.38) because of the difference in refractive indices.

Scattering tissue models were developed to determine if the contrast agents could be detected in an environment similar to biological tissues. These models consisted of agarose gelatin in which skim milk was added as a scatterer to achieve a reduced scattering coefficient of 15–25 cm$^{-1}$ at 800 nm wavelength, which is comparable to that measured in human epidermal tissue [18]. The reduced scattering coefficients for each model were measured by oblique-incidence fiber-optic reflectometry [62]. Tissue models were prepared by heating a solution of agarose and water near boiling and adding approximately 25% milk by volume to achieve the desired scattering properties. The agarose-milk solution was cooled to form a scattering layer. On top of this layer, a 50 µL drop of microparticles ($1.3 \times 10^5$ microparticles/µL)) and gelatin was deposited and cooled. A second agarose-milk scattering layer up to 1 mm thick was added over the surface to obscure the contrast agents. These samples were made in 5 cm diameter glass dishes and were 1–2 cm deep.

Tissue model samples were imaged with a fiber-optic based OCT system. The broad-bandwidth optical source consisted of a Nd:YVO$_4$ diode-pumped titanium:sapphire laser which produced 500 mW average power and approximately 90 fs pulses with an 80 MHz repetition rate at 800 nm center wavelength. About 350 mW of this power was coupled into a single mode fiber and was split into two paths by a broadband 50:50 fiber coupler (Gould Fiber Optics, Inc.). When passed through this coupler, the spectral bandwidth of the pulse broadened from 25 to 50 nm FWHM. The axial and transverse resolutions of the system were 6 µm and 14 µm, respectively. The reference arm of the OCT interferometer contained a galvanometer-driven retroreflector delay line that was scanned a distance of 5 mm at a rate of 30 Hz to provide axial reflectance data. The sample arm consisted of a fiber-optic collimator to produce a 2 mm diameter beam from the fiber. The beam was focused into the tissue by a 12.5 mm diameter, 30 mm focal length achromatic lens. The beam was scanned over the tissue with a pair of orthogonal galvanometer-controlled mirrors. Approximately 6 mW of power was incident on the tissue. The reflected light was recollected by the lens and collimator and recombined in the fiber coupler with the delayed reference signal. The interference signal was measured by a silicon photodiode, bandpass-filtered by an analog filter, and rectified by a logarithmic envelope detection circuit. The resulting scattering magnitude was digitized to 12-bit accuracy. Adjacent axial scans were assembled to produce two-dimensional OCT images that were displayed on the computer using custom data acquisition and display software.

FIGS. 7(a) and 7(b) show OCT images (500×500 pixel, 3×5 mm) of the logarithmic reflectance signal measured from a tissue model without and with air-filled microparticle contrast agents, respectively. Both samples were prepared by depositing two separate layers of agarose-milk ($\mu_s$'=20 cm$^{-1}$). The sample shown in FIG. 7(b) had a thin layer of contrast agents deposited between the layers. The contrast agents had a size distribution given by FIG. 2 and were diluted to 60% by volume with a mixture of agarose and 25% milk to suspend the contrast agents. Because no boundary is visible in FIG. 7(a), it was concluded that the scattering in FIG. 7(b) is due to contrast agents and not the sample preparation method. FIG. 7(c) is a series of plots of the average scattering intensity as a function of depth (averaged over 75 axial scans) for the five boxed regions in FIGS. 7(a) and 7(b). The axial depth in the tissue model was scaled by the reciprocal of the refractive index of the agarose-milk gel (n=1.31). The optical backscatter intensity is normalized by the magnitude of the scattering near the surface to account for variations in intensity due to the scanning angle of the OCT beam. The control region is from the sample without contrast agents to show that the backscatter ratio remains under one. The other four regions are from the sample containing contrast agents at increasing depths under the surface. Samples 1, 2, and 3 have peak backscatter ratios near 2.0, which indicate that the contrast is 2:1 over the background. Sample 4 is slightly decreased, showing that the signal is decreasing at that depth (approximately 650 µm). This suggests that this particular sample and concentration of contrast agents may not provide a useful signal at depths significantly greater than 700–800 µm. Because the scattering properties of the microparticles can be manipulated by changing the size distribution and by encapsulating scattering particles, higher contrast should be possible.

REFERENCES

1. Langer R. Drug delivery and targeting. Nature 392: S5–10, 1998.
2. Christiansen C, Kryvi H, Sontum P C, Skotland T. Physical and biochemical characterization of Albunex, a new ultrasound contrast agent consisting of air-filled albumin microparticles suspended in a solution of human albumin. Biotechnol. Appl. Biochem. 19:307–320, 1994.
3. Grinstaff M W, Suslick K S. Proteinaceous microbubbles: synthesis of an echo contrast agent. Proc. Natl. Acad. Sci. USA 88:7708–7710, 1991.
4. Geny B, Bischoff P, Muan B, Piquard F, Thiranos J C, Epailly E, Lambrechs M, Juelsrud-Vebner A, Eisenmann B, Haberey P. Safety of a new transpulmonary echocontrast agent (Albunex) in repeated echocardiographic studies in patients. Clin. Cardiol. 20:111–115, 1997.
5. Suslick K S, Grinstaff M W. Protein microencapsulation of nonaqueous liquids. J. Am. Chem. Soc. 112:7807–7809, 1990.
6. Webb A G, Wong M, Kolbeck K J, Magin R L, Wilmes L J, Suslick K S. Sonochemically produced fluorocarbon microparticles: a new class of MRI contrast agents. J. Mag. Res. Imaging. 6:675–683, 1996.
7. Desai N P, Soon-Shiong P, Grinstaff M W, Yao Z, Sandford P A, Suslick K S. Controlled and targeted drug delivery with biocompatible protein shell microparticles. Proc. Soc. Biomaterial 20:112, 1994.
8. Liu K J, Grinstaff M W, Jiang J, Suslick K S, Swartz H M, Wang W. In vivo measurement of oxygen concentration using sonochemically synthesized microparticles. Biophys. J. 67:896–901, 1994.
9. Wong M, Suslick K S. Sonochemically produced hemoglobin microbubbles. *Hollow and Solid Spheres and Microparticles* Wilcox D L, et. al., eds. Matl. Res. Soc., Pittsburgh, pp 89–94, 1995.
10. Dick A, Adam G, Tacke J, Prescher A, Southon T E, Gunther R W. Computed tomography of experimental liver abcesses using a new liposomal contrast agent. Invest. Radiology 31:194–203, 1996.
11. Gram T E. Drug absorption and distribution. In *Modern Pharmacology with Clinical Applications*. Craig C R, Stitzel R E, eds. Little, Brown, and Co., Inc., Boston, pp. 13–24. 1997.
12. Lasic DD, Papahadjopoulos D. Liposomes revisited. Science 267:1275–1276, 1995.
13. Suslick K S. Sonochemistry. Science 247:1439, 1990.
14. McNamara III W B, Didenko Y, Suslick K S. Sonoluminescence temperatures during multibubble cavitation. Nature 401:772–775, 1999.
15. Huang D, Swanson E A, Lin C P, Schuman J S, Stinson W G, Chang W, Hee M R, Flotte T, Gregory K, Puliafito C A, Fujimoto J G. Optical Coherence Tomography. Science 254:1178–1181, 1991.
16. Fujimoto J G, Brezinski M E, Tearney G J, Boppart S A, Bouma B E, Hee M R, Southern J F, Swanson E A. Biomedical imaging and optical biopsy using optical coherence tomography. Nature Medicine 1:970–972, 1995.
17. Brezinski M E, Tearney G J, Bouma B E, Izatt J A, Hee M R, Swanson E A, Southern J F, Fujimoto J G. Optical coherence tomography for optical biopsy: properties and demonstration of vascular pathology. Circulation 93:1206–1213, 1996.
18. Schmitt J M, Knuttel A, Bonner R F. Measurements of optical properties of biological tissues by low-coherence reflectometry. Appl. Opt. 32:6032–6042, 1993.
19. Sergeev A M, Gelikonov V M, Gelikonov G V, Feldchtein F I, Kuranov R V, Gladkova N D. In vivo endoscopic OCT imaging of precancer and cancer states of human mucosa. Opt. Express 1:432–440, 1997.
20. Tearney G J, Brezinski M E, Bouma B E, Boppart S A, Pitris C, Southern J F, Fujimoto J G. In vivo endoscopic optical biopsy with optical coherence tomography. Science. 276:2037–2039, 1997.
21. Boppart S A, Bouma B E, Pitris C, Tearney G J, Southern J F, Brezinski M E, Fujimoto J G. Intraoperative assessment of microsurgery with three-dimensional optical coherence tomography. Radiology. 208:81–86, 1998.
22. Hee M R, Izatt J A, Swanson E A, Huang D, Schuman J S, Lin C P, Puliafito C A, Fujimoto J G. Optical coherence tomography of the human retina. Arch. Ophthalmol. 113: 325–332, 1995.
23. Puliafito C A, Hee M R, Lin C P, Reichel E, Schuman J S, Duker J S, Izatt J A, Swanson E A, Fujimoto J G. Imaging of macular disease with optical coherence tomography (OCT). Ophthalmology 102:217–229, 1995.
24. Puliafito C A, Hee M R, Schuman J S, Fujimoto J G. *Optical Coherence Tomography of Ocular Diseases*. Slack, Inc, Thorofare, N.J., 1995.
25. Schmitt J M, Knuttel A, Yadlowsky M, Eckhaus A A. Optical coherence tomography of a dense tissue: statistics of attenuation and backscattering. Phys. Med. Biol. 39:1705–1720, 1994.
26. Schmitt J M, Yadlowsky M J, Bonner R F. Subsurface imaging of living skin with optical coherence microscopy. Dermatology 191:93–98, 1995.
27. Sergeev A M, Gelikonov V M, Gelikonov G V, Feldchtein F I, Kuranov R V, Gladkova N D, Shakhova N M, Snopova L B, Shakov A V, Kuznetzova I A, Denisenko A N, Pochinko V V, Chumakov Y P, Streltzova O S. In vivo endoscopic OCT imaging of precancer and cancer states of human mucosa. Opt Express 1:432–440, 1997.

28. Profio A E, Doiron D R. Transport of light in tissue in photodynamic therapy of cancer. Photochem. Photobiol. 46:591–599, 1987.

29. Tearney G J, Brezinski M E, Boppart S A, Bouma B E, Weissman N, Southern J F, Swanson E A, Fujimoto J G. Catheter-based optical imaging of a human coronary artery. Circulation 94:3013, 1996.

30. Tearney G J, Brezinski M E, Southern J F, Bouma B E, Boppart S A, Fujimoto J G. Optical biopsy in human gastrointestinal tissue using optical coherence tomography. Amer. J. Gastroenterol. 92:1800–1804, 1997.

31. Tearney G J, Brezinski M E, Southern J F, Bouma B E, Boppart S A, Fujimoto J G. Optical biopsy in human urologic tissue using optical coherence tomography. J. Urol. 157:1915–1919, 1997.

32. Boppart S A, Brezinski M E, Pitris C, Fujimoto J G. Optical Coherence Tomography for Neurosurgical Imaging of Human Intracortical Melanoma. Neurosurgery 43:834–841, 1998.

33. Bouma B E, Tearney G J, Boppart S A, Hee M R, Brezinski M E, Fujimoto J G. High resolution optical coherence tomographic imaging using a modelocked Ti:$Al_2O_3$ laser. Opt. Lett. 20:1486–1488, 1995.

34. Drexler W, Morgner U, Kartner F X, Pitris C, Boppart S A, Li X, Ippen E P, Fujimoto J G. In vivo ultrahigh resolution optical coherence tomography. Opt. Lett. 24:1221–1223, 1999.

35. Tearney G J, Bouma B E, Boppart S A, Golubovic B, Swanson E A, Fujimoto J G. Rapid acquisition of in vivo biological images using optical coherence tomography. Opt. Lett. 21:1408–1410, 1996.

36. Chen Z, Milner T E, Srinivas S, Wang X. Noninvasive imaging of in vivo blood flow velocity using optical Doppler tomography. Opt. Lett. 22:1119–1121, 1997.

37. Yazdanfar S, Kulkarni M D, Izatt J A. High resolution imaging of in vivo cardiac dynamics using color Doppler optical coherence tomography. Opt. Express. 1:424–431, 1997.

38. de Boer J F, Milner T E, van Germert M J C, Nelson S J. Two-dimensional birefringence imaging in biological tissue by polarization sensitive optical coherence tomography. Opt. Lett. 22:934–936, 1997.

39. Tearney G J, Boppart S A, Bouma B E, Brezinski M E, Weissman N J, Southern J F, Fujimoto J G. Scanning single-mode fiber optic catheter-endoscope for optical coherence tomography. Opt. Lett. 21:1–3, 1996.

40. Boppart S A, Bouma B E, Pitris C, Tearney G J, Fujimoto J G. Forward-imaging instruments for optical coherence tomography. Opt. Lett. 22:1618–1620, 1997.

41. Tearney G J, Brezinski M E, Bouma B E, Boppart S A, Pitris C, Southern J F, Fujimoto J G. In vivo endoscopic optical biopsy with optical coherence tomography. Science 276:2037–2039, 1997.

42. Bouma B E, Tearney G J, Compton C C, Nishioka N S. High-resolution imaging of the human esophagus and stomach in vivo using optical coherence tomography. Gastrointest. Endosc. 51:467–474, 2000.

43. Sivak M V Jr, Kobayashi K, Izatt J A, Rollins A M, Ung-Runyawee R, Chak A, Wong R C, Isenberg G A, Willis J. High-resolution endoscopic imaging of the gastrointestinal tract using optical coherence tomography. Gastrointest. Endosc. 51:474–479, 2000.

44. Li X, Boppart S A, Van Dam J, Mashimo H, Mutinga M, Drexler W, Klein M, Pitris C, Krinsky M L, Brezinski M E, Fujimoto J G. Optical coherence tomography: advanced technology for the endoscopic imaging of Barrett's esophagus. Endoscopy 32:921–930, 2000.

45. Boppart S A, Brezinski M E, Bouma B E, Tearney G J, Fujimoto J G. Investigation of developing embryonic morphology using optical coherence tomography. Dev. Biol. 177:54–63, 1996.

46. Boppart S A, Brezinski M E, Tearney G J, Bouma B E, Fujimoto J G. Imaging developing neural morphology using optical coherence tomography. J. Neurosci. Meth. 2112:65–72, 1996.

47. Boppart S A, Tearney G J, Bouma B E, Southern J F, Brezinski M E, Fujimoto J G. Noninvasive assessment of the developing Xenopus cardiovascular system using optical coherence tomography. Proc. Natl. Acad. Sci. USA 94:4256–4261, 1997.

48. Boppart S A, Bouma B E, Pitris C, Southern J F, Brezinski M E, Fujimoto J G. In vivo cellular optical coherence tomography imaging. Nature Med. 4:861–864, 1998.

49. Pitris C, Goodman A K, Boppart S A, Libus J J, Fujimoto J G, Brezinski M E. High resolution imaging of gynecological neoplasms using optical coherence tomography. Obstet. Gynecol. 93:135–139, 1999.

50. Pitris C, Jesser C, Boppart S A, Stamper D, Brezinski M E, Fujimoto J G. Feasibility of optical coherence tomography for high resolution imaging of human gastrointestinal tract malignancies. J. Gastroenterol. 35:87–92, 1999.

51. Boppart S A, Brezinski M E, Pitris C, Fujimoto J G. "Optical coherence tomography for neurosurgical imaging of human intracortical melanoma," Neurosurgery 43:834–841, 1998.

52. van der Laan B F, Jansen G, Kathmann G A, Westerhof G R, Schornagel J H, Hordijk G J. In vitro activity of novel antifolates against human squamous carcinoma cell lines of the head and neck with inherent resistance to methotrexate. Int. J. Cancer 30:909–914,1992.

53. Mathias C J, Wang S, Lee R J, Waters D J, Low P S, Green M A. Tumor-selective radiopharmaceutical targeting via receptor-mediated endocytosis of gallium-67-deferoxamine-folate. J. Nucl. Med. 37:1003–1008, 1996.

54. Lee R J, Low P S. Delivery of liposomes into cultured KB cells via folate receptor-mediated endocytosis. J. Biol. Chem. 269:3198–3204, 1994.

55. Burns R A, Klaunig J E, Shulok J R, Davis W J, Goldblatt P J. Tumor-localizing and photosensitizing properties of hematoporphyrin derivative in hamster buccal pouch carcinoma. Oral Surg. Oral Med. Oral Pathol. 61:368–372, 1986.

56. Korbelik M, Krosl G. Photofrin accumulation in malignant and host cell populations of various tumors. Br. J. Cancer 73:506–513, 1996.

57. Gazelle G S, Wolf G L, McIntire G L, Bacon E R, Halpern E F, Cooper E R, Toner J L. Nanoparticulate computed tomography contrast agents for blood pool and liver-spleen imaging, Acad. Radiol. 1, 373–376, 1994.

58. Su M Y, Muhler A, Lao X, Nalcioglu O. Tumor characterization with dynamic contrast-enhanced MRI using MR contrast agents of various molecular weights, Magn. Reson. Med. 39, 259–269, 1998.

59. Bugaj J E, Achilefu S, Dorshow R B, Rajagopalan R. Novel fluorescent contrast agents for optical imaging of in vivo tumors based on a receptor-targeted dye-peptide conjugate platform, J. Biomed. Opt. 6, 122–133, 2001.

60. Barton J K, Hoying J B, Sullivan C J. Use of microbubbles as an optical coherence tomography contrast agent, Contrast Material Research Conference, Woodstock, Vt. (published in supplement to "Academic Radiology," Sep. 12–17, 1999).

61. Eppstein D A, Fraser-Smith E B, Mattews T R. U.S. Pat. No. 4,522,811. Serial injection of muramyldipeptides and liposomes enhances the anti-infective activity of muramyldipeptides 1985.

62. Wang L, Jacques, S L. Use of a laser beam with an oblique angle of incidence to measure the reduced scattering coefficient of a turbid medium, Appl. Opt. 34:2362–2366, 1995.

The invention claimed is:

1. In a method of forming an image by optical coherence tomography, including exposing a patient to electromagnetic radiation, collecting reflected electromagnetic radiation, and forming an image from the collected electromagnetic radiation, the improvement comprising administering a contrast agent to the patient to enhance contrast of the image,
wherein the contrast agent comprises microparticles comprising a surface coat, and
the microparticles comprise cross-linked protein.

2. The method of claim 1, wherein the contrast agent comprises microparticles further comprising:
an inner core comprising a charged or magnetic pigment or dye.

3. The method of claim 1, wherein the surface coat comprises polyethylene glycol.

4. A method of forming an image of a sample, comprising:
forming an image of a mixture, by exposing the mixture to electromagnetic radiation;
wherein the mixture comprises the sample and microparticles,
the microparticles further comprise a surface coat, and
the electromagnetic radiation is in the frequency range of infra-red to ultraviolet light.

5. The method of claim 4, wherein the forming of the image is by a method selected from the group consisting of optical coherence tomography, light microscopy, holography, confocal microscopy, polarization microscopy, interference microscopy, multi-photon microscopy, and endoscopy.

6. The method of claim 4, wherein the forming of the image is by optical coherence tomography.

7. The method of claim 4, wherein the microparticles comprise cross-linked protein.

8. The method of claim 4, wherein the surface coat comprises at least one member selected from the group consisting of polyethylene glycol, antibodies, membrane receptor ligands, colloids, and particles.

9. The method of claim 8, wherein
the colloids are silica, gold, or silver colloids, and
wherein the particles are melanin, iron or carbon.

10. The method of claim 6, wherein the surface coat comprises polyethylene glycol.

11. The method of claim 6, wherein the surface coat comprises antibodies.

12. The method of claim 4, wherein the microparticles further comprise an inner core comprising solid, liquid, or solid and liquid.

13. The method of claim 4, wherein the microparticles further comprise a dye or pigment.

14. The method of claim 13, wherein the dye or pigment is charged or magnetic.

15. The method of claim 14, further comprising exposing the sample to an alternating electric or magnetic field.

16. The method of claim 5, wherein the sample is a patient.

17. The method of claim 6, wherein the sample is a human patient.

18. A method of forming an image of a sample, comprising:
forming an image of a mixture, by exposing the mixture to electromagnetic radiation;
wherein the mixture comprises the sample and microparticles,
the microparticles further comprise a surface coat,
the electromagnetic radiation is in the frequency range of infra-red to ultraviolet light,
the forming of the image is by optical coherence tomography, and
the surface coat comprises polyethylene glycol.

19. The method of claim 18, wherein the microparticles comprise cross-linked protein.

20. The method of claim 18, wherein the microparticles further comprise an inner core comprising solid, liquid, or solid and liquid.

21. The method of claim 18, wherein the microparticles further comprise a dye or pigment.

22. The method of claim 21, wherein the dye or pigment is charged or magnetic.

23. The method of claim 22, further comprising exposing the sample to an alternating electric or magnetic field.

24. The method of claim 18, wherein the sample is a patient.

25. The method of claim 18, wherein the sample is a human patient.

* * * * *

UNITED STATES PATENT AND TRADEMARK OFFICE
CERTIFICATE OF CORRECTION

PATENT NO. : 7,198,777 B2
APPLICATION NO. : 10/463835
DATED : April 3, 2007
INVENTOR(S) : Stephen A. Boppart et al.

It is certified that error appears in the above-identified patent and that said Letters Patent is hereby corrected as shown below:

On the Title Page item 56 under Other Publications

Line 33, please insert a quotation mark before "Noninvasive".
Line 34, please insert a quotation mark after "tomography,".

Page 2 item 56 under Other Publications

Col. 1, line 11, please insert a space after "ence".
Col. 2, line 46, please delete "722" and insert --772--.

Page 3 item 56 under Other Publications

Col. 1, line 38, please insert a quotation mark before "Rapid".
Col. 1, line 39, please insert a quotation mark after "tomography,".

Signed and Sealed this

Twenty-seventh Day of November, 2007

JON W. DUDAS
*Director of the United States Patent and Trademark Office*